US005656037A

United States Patent [19]
Vigo et al.

[11] Patent Number: 5,656,037
[45] Date of Patent: Aug. 12, 1997

[54] REACTION PRODUCTS OF MAGNESIUM ACETATE AND HYDROGEN PEROXIDE FOR IMPARTING ANTIBACTERIAL ACTIVITY TO FIBROUS SUBSTRATES

[75] Inventors: Tyrone L. Vigo; Gary F. Danna, both of New Orleans, La.

[73] Assignee: The United States of America as represented by the Secretary of Agriculture, Washington, D.C.

[21] Appl. No.: 580,230

[22] Filed: Dec. 28, 1995

[51] Int. Cl.[6] .................... D06L 3/02; B05D 1/18; C01F 5/00; C07F 3/02
[52] U.S. Cl. ................ 8/111; 8/116.1; 8/115.68; 8/115.69; 8/137; 252/186.26; 252/186.27; 427/212; 427/384; 427/394; 427/430.1; 427/331; 427/379; 428/907; 428/361; 428/365; 428/375; 556/1; 423/583; 423/635; 423/636; 442/123; 442/361; 442/414
[58] Field of Search .............. 8/111, 116.1, 115.68, 8/115.69, 137; 252/8.6, 8.9, 95, 174.25, 173, 186.26, 186.27; 423/583, 635, 636; 427/394, 354, 381, 2.12, 384, 430.1, 331, 379; 428/224, 392, 393, 264, 262, 261, 260, 240, 289, 288, 907, 357, 361, 365, 375; 556/1

[56] References Cited

U.S. PATENT DOCUMENTS

| | | |
|---|---|---|
| 4,115,422 | 9/1978 | Welch et al. |
| 4,172,841 | 10/1979 | Danna et al. |
| 4,174,418 | 11/1979 | Welch et al. |
| 4,199,322 | 4/1980 | Danna et al. .............................. 8/186 |
| 5,464,563 | 11/1995 | Moore et al. .............................. 8/111 |

OTHER PUBLICATIONS

Derwent abstract no. 92–297506 for SU 1683763. Nov. 1993.

Primary Examiner—Alan D. Diamond
Attorney, Agent, or Firm—M. Howard Silverstein; Joseph A. Lipovsky; John D. Fado

[57] ABSTRACT

The preparation of water-insoluble, bactericidal, peroxide-containing products, by reaction of magnesium acetate with hydrogen peroxide, and products obtained are disclosed. Processes for application and deposition of these reaction products on natural, synthetic and blend fibrous substrates are also disclosed. The modified fibrous substrates thus produced inhibit the growth and spread of odor- and disease-causing gram-positive and gram-negative bacteria and the antibacterial activity of the modified fibrous substrates is durable to repeated launderings.

21 Claims, No Drawings

REACTION PRODUCTS OF MAGNESIUM ACETATE AND HYDROGEN PEROXIDE FOR IMPARTING ANTIBACTERIAL ACTIVITY TO FIBROUS SUBSTRATES

BACKGROUND OF THE INVENTION

1. Field of the Invention

This invention relates to magnesium peroxyacetate and magnesium dihydroperoxide products that can be used to impart antibacterial activity to fibrous substrates.

2. Description of Related Art

Many types of antibacterial agents have been applied to fibrous substrates. However, there are very few agents that retain their germicidal activity after repeated laundering, pose no environmental problems, do not cause undesirable side effects to either the substrate or user thereof, and are inexpensive to manufacture.

Hydrogen peroxide is well known as a safe and effective topical disinfectant and antiseptic that is applied as a dilute aqueous solution to cleanse wounds. However, it has no substantivity to fibrous materials and is readily removed from fabrics or fibrous assemblies by a single wash.

Welch et al., in U.S. Pat. Nos. 4,115,422 and 4,174,418, describe the durable antibacterial effects of water-insoluble complexes of hydrogen peroxide/zirconyl acetate and Danna et al. in U.S. Pat. Nos. 4,172,841 and 4,199,322 describe the durable antibacterial effects of water-insoluble complexes of hydrogen peroxide/zinc acetate. However, each of these systems has several limitations, deficiencies, and disadvantages.

The hydrogen peroxide/magnesium acetate reaction products of the present invention differ from the hydrogen peroxide complexes with zirconyl acetate and zinc acetate of the prior art in terms of their preparation, composition, stability, and application to fibrous substrates.

Zirconyl acetate/hydrogen peroxide complexes require the presence of appreciable amounts of acetic acid in solution for their preparation. Omission of the acetic acid from the preparation process causes exothermic gel formation with concomitant loss of peroxide oxygen or bound peroxide in the complexes. This acetic acid is also requisite for in situ application of the reaction mixture (acetic acid, zirconyl acetate, and hydrogen peroxide) to fibrous substrates in order to obtain suitable amounts of bound peroxide (peroxide oxygen) after appropriate drying and curing.

Other limitations of the zirconyl acetate/hydrogen peroxide complexes of Welch et al. include:

(a) a 24 hour time limitation between preparation of the reaction mixture and its application to fibrous substrates in order to affix antibacterial amounts of peroxide oxygen;

(b) a cure temperature limitation of 140° C. to avoid thermal degradation of the complex; and (c) the causation of unacceptable weight gains (>15% by wt.), increased fabric stiffness and decreased wettability when obtaining oxygen contents as low as 0.3% on modified fibrous substrates. Such decreased wettability substantially reduces or nullifies the antibacterial activity of the modified fibrous substrates owing to the lack of adequate moisture for transport of the peroxide oxygen to the bacteria.

Similar limitations and disadvantages are observed with the hydrogen peroxide/zinc acetate complexes of Danna et al. and their durable application to fibrous substrates. Effective formation of these complexes likewise requires the presence of acetic acid; this component is also necessary in conjunction with hydrogen peroxide and zinc acetate for in situ application of the complexes to fibrous substrates in a form which provides peroxide oxygen or bound peroxide.

As in the case of the Welch et al.'s hydrogen peroxide/zirconyl acetate complexes, solutions containing Danna et al.'s hydrogen peroxide/zinc acetate complexes rapidly lose their peroxide oxygen available for binding to fibrous substrates if the solutions are not used within 48–72 hours.

Cure temperatures are also limited to a maximum of 140° C. due to irreversible decomposition, which occurs with these and most peroxide species immediately above this threshold.

A further disadvantage for these prior art complexes is that, once formed, their relative insolubility precludes their practical reuse for application to fibrous substrates.

It is also well known that a simple, water-insoluble peroxide of magnesium having the formula $MgO_2$ can be prepared by adding solid magnesium oxide to a solution of hydrogen peroxide. This product is similar to the starting material (magnesium oxide) in its appearance and physical properties but is not colloidally dispersible in aqueous media (R. E. Hall, *Ency. Chem. Tech.* Vol. 17, p. 4 (1971)).

SUMMARY OF THE INVENTION

The present invention relates to water-dispersible reaction products that are hydrolytically stable at ambient temperatures and thermally stable up to about 350° C. These reaction products, which possess peroxide oxygen contents ranging from about 1% to about 30%, are prepared using hydrogen peroxide and magnesium acetate (anhydrous or tetrahydrate) in mole ratios ranging from about 2:1 to about 40:1.

The present invention further relates to processes for applying the above reaction products as aqueous dispersions optionally containing hydrogen peroxide, or as foams in aqueous hydrogen peroxide, to impart antibacterial activity to natural and synthetic fibrous substrates of all major fiber types, including cellulose, wool, polyester, polyamide, polypropylene, glass, and blends thereof.

The fibrous substrates are treated with such aqueous dispersions or foams wherein the reaction products of the invention are present in amounts ranging from about 10% to about 17% by weight. Upon subsequent heating, washing, and drying, the modified fibrous substrates contain durably bound peroxide oxygen and/or peroxide and exhibit antibacterial activity resistant to repeated laundering.

More particularly, the present invention relates to a process for the preparation of stable, water insoluble, water-dispersible products resulting from the reaction of magnesium acetate and hydrogen peroxide comprising:

(a) preparing an aqueous solution comprising from about 15% to about 29% by weight hydrogen peroxide and from about 5% to about 50% by weight magnesium acetate (based on the tetrahydrate), and (b) removing the solvent to yield a solid product comprising magnesium peroxyacetate, magnesium dihydroperoxide, or a combination thereof, said product containing peroxide oxygen.

Optionally, the process can include the further steps of washing, drying and filtering the solid product.

In another aspect, the present invention relates to a process for rendering a fibrous substrate bacteriostatic and/or bactericidal comprising:

(a) immersing the fibrous substrate in an aqueous dispersion comprising from about 10% to about 17% by weight of the magnesium peroxy-containing reaction product of the instant invention and from about 0% to about 27% by weight of hydrogen peroxide;

(b) optionally, removing excess dispersion from the fibrous substrate; and (c) drying the fibrous substrate, whereby the peroxy-containing magnesium composition is deposited on the substrate.

Optionally, this process can include the further steps of washing and drying the treated fibrous substrate.

The present invention also relates to novel compositions of matter comprising magnesium peroxyacetate and magnesium diperoxide.

DESCRIPTION OF THE PREFERRED EMBODIMENTS

The processes of the present invention, and products thereof, are based on the discovery that magnesium acetate, under the proper conditions, forms previously unknown water-dispersible products when reacted with hydrogen peroxide. These reaction products are both more thermally and hydrolytically stable and contain higher amounts of bound peroxide and acetate than do the hydrogen peroxide/zirconyl acetate and hydrogen peroxide/zinc acetate complexes known heretofore.

The reaction products are thermally stable up to about 350° C., in contrast to the much lower decomposition temperatures of the corresponding zirconyl and zinc peroxide complexes (225° C. or less).

The magnesium acetate-hydrogen peroxide reaction products can be prepared as solid products and stored indefinitely. Alternatively, they can be dispersed in water, forming a hydrosol, for several months before their application to fibrous substrates. When stored and subsequently affixed to substrate, at least about 85% of the peroxide oxygen is affixed. When the originally prepared dispersion is used immediately, substantially 100% of the peroxide oxygen is affixed to the substrate.

In contrast, the solid zirconyl acetate/hydrogen peroxide and zinc acetate/hydrogen peroxide complexes of the prior art are incapable of forming a hydrosol. Furthermore, these complexes cannot be dissolved from solid form and applied to fibrous substrates to impart antibacterial activity, but can only be applied from the initially prepared solution, with this having to be done within 72 hours of their preparation.

No method has heretofore been known for either the creation of the water-dispersible reaction products of the invention, or their use for the impregnation of fibrous substrates to give a durable, uniform, non-dusting fixation to the fibers. The magnesium peroxy reaction products of the present invention contain significant proportions of acetate groups, as indicated by chemical analysis, and differ in this respect from the simple magnesium peroxides of the prior art.

The prior art offers no means of preparing stable water-dispersible colloids of magnesium peroxide that produce modified fibrous materials with uniform distribution of bound peroxide or peroxide oxygen. This contrasts with the products of the present invention which can be affixed to a fibrous substrate by removal of water or solvent. The bound magnesium peroxy moieties impart antibacterial activity through repeated launderings.

The maximum thermal decomposition temperature for the products of the present invention is as much as 200° C. higher than the upper limit of 140° C. employed for fixation of solutions of zirconyl acetate/hydrogen peroxide and zinc acetate/hydrogen peroxide complexes. Fixation above 140° C. with the latter two complexes results in destruction of the peroxide oxygen and the failure to impart any level of antibacterial activity to the fibrous substrate.

In the processes of the present invention, the magnesium acetate used can be either in the anhydrous state or in the form of the more readily available tetrahydrate having the formula $Mg(OOCCH_3)_2 \cdot 4H_2O$. In the descriptions that follow, however, all percentages are by weight and refer to the tetrahydrate compounds, except where specifically stated otherwise.

The processes of the present invention are based on the discovery that magnesium acetate reacts with hydrogen peroxide in aqueous media to form solid, colorless, water-insoluble products that form stable, water dispersible colloids. These reaction products, as determined by elemental and thermal analysis and infrared spectroscopy, correspond to the structures:

(I)

(II)

and

(III)

which are herein named magnesium diacetate, magnesium peroxyacetate and magnesium dihydroperoxide respectively.

The specific products and their relative amounts varies with the proportion or ratio of reactants used. At molar ratios of 2:1 for hydrogen peroxide to magnesium acetate the product profile is approximately 50% by weight magnesium diacetate and 50% magnesium peroxyacetate. With a 40:1 molar ratio for the same reactants, this profile shifts to a product makeup of 30% by weight of magnesium peroxyacetate and 70% of magnesium dihydroperoxide. The reaction of magnesium acetate and hydrogen peroxide proceeds to completion only if the aqueous solution is evaporated to leave a completely dry residue. Optional use of elevated temperatures (up to 200° C.) and/or reduced pressures (as low as 0.1 atmosphere) may be used to accelerate this process.

The hydrogen peroxide used in the reaction with magnesium acetate may be in the form of an aqueous solution containing from about 3% to about 90% hydrogen peroxide by weight with an amount ranging from about 20% to about 50% being preferred. The use of more dilute solutions requires larger solution volumes and, accordingly, longer reaction times and higher reaction temperatures to effect solvent removal and completion of the reaction. Conversely, the use of more concentrated solutions requires smaller solution volumes, shorter reaction times and lower reaction temperatures.

As in the preparation of most peroxides, ignition may occur with the use of high peroxide concentrations and high temperatures. Therefore, when aqueous hydrogen peroxide is utilized in concentrations equal to or greater than 30% by weight, temperatures in excess of 90° C. should not be used in removing the last 25% of the volatiles. Once the product is nearly completely dry, as indicated by there being no soft or moist regions upon probing with a spatula, the temperature can be increased to up to 200° C. for 5 minutes (or to an equivalent time/temperature combination) to ensure complete dryness. This is done so as to prevent the potential for decomposition of the magnesium peroxy-reaction products when they are reintroduced into aqueous solution.

Products derived from the reaction of hydrogen peroxide with magnesium acetate have peroxide oxygen contents ranging from about 1 to about 30% by weight; this being accomplished by using mole ratios in the range of from 2:1 to 40:1 hydrogen peroxide:magnesium acetate in the initial reaction solution.

The present invention also includes the preparation of bacteriostatic and bactericidal fibrous substrates or textiles from the hydrogen peroxide:magnesium acetate reaction products of this invention. This process comprises the steps of:

(a) immersing a natural and/or synthetic fibrous substrate in an aqueous bath that contains from about 10% to about 17% by weight of the magnesium peroxy-containing reaction product of the instant invention and from about 0 to about 27% by weight of hydrogen peroxide, (b) optionally removing bath solution in excess of a wet pickup rate ranging from about 10% to about 200% (wt. solution/wt. substrate), and (c) drying the fibrous substrate by means of heating such to a temperature ranging from about 80° C. to about 200° C. for an inversely proportional amount of time ranging from about 5 to about 1.5 minutes, thereby effecting deposition of the magnesium peroxy-reaction products thereon.

In a preferred embodiment, the process can include the further steps of:

(d) washing the fibrous substrate to remove excess reagents, and (e) drying the washed substrate at a temperature ranging from about 50° C. to about 200° C. for an inversely proportional amount of time ranging from about 1 hour to about 0.5 minute.

In step (a) of the above process, the magnesium peroxy-reaction products are dispersed in water or aqueous hydrogen peroxide. Water is the preferred solvent due to its simplicity of use, minimal expense and ready availability. Further inclusion of hydrogen peroxide in the solvent system may however be desired when a one step sterilization bath for the fibrous substrate is desirable or when it is intended to apply the reaction products in the form of a foam. Usable solution concentrations of hydrogen peroxide range from about 3% to about 30% by weight, with a preferred range of from about 15% to about 30% by weight.

Preferably, the magnesium peroxy-reaction products possess peroxide oxygen contents ranging from about 5% to about 30%. These are derived from preparations wherein the molar proportion of hydrogen peroxide:magnesium acetate ranges from about 7:1 to about 30:1.

In carrying out step (a), the fibrous substrate can be threads, roving, yarn, or fabric in a woven, knit, and/or nonwoven construction. The fibrous substrate can be natural; e.g., wool or cellulose, in the form of textile fiber, or short fiber, such as paper derived from wood pulp; or a synthetic fiber, such as polyester, polyamide, polypropylene, glass or any other major fiber type, or blends of any of the foregoing.

In step (b), excess bath solution can be removed from the substrate. This can be accomplished by ordinary mechanical methods, such as by squeezing through rolls, centrifuging, or draining.

In step (c), the impregnated fibrous substrate is heated to drive off the water, whereby the water dispersible magnesium peroxy-reaction product will be deposited onto the fibrous substrate, from which it will be slowly released during repeated laundering. Heating can be carried out in an oven, preferably one having forced draft air directed at the surface of the fibrous substrate and exhausting through a vent to remove fumes when hydrogen peroxide is present. Such venting is unnecessary when water alone is used.

In step (d), the treated fibrous substrate can be washed with either hot or cold water. The magnesium peroxyacetate products are water insoluble and durable to the mechanical agitation, spraying, and rubbing that occurs in washing machines or batch textile washing equipment.

The final drying step (e) can be carried out by any ordinary means, such as oven drying, line drying, or tumble drying, as in a mechanical clothes dryer. Drying temperatures ranging from about 80° C. to about 200° C. for an inversely proportional amount of time ranging from about 6 to about 1.5 minutes, are preferred.

As an alternative to the above fibrous substrate modification process, a foam can be prepared for coating onto the surface of the fibrous substrate. In alternative step (a), the preferred magnesium peroxy-reaction products are dispersed into an aqueous hydrogen peroxide solution to prepare a foam. These products correspond to peroxide oxygen contents in the range of about 1% to about 30%, with a preferred range of about 5% to about 30%. It is preferred to have about 10–20% by weight of these products dispersed in an aqueous solution containing from about 10% to about 30% hydrogen peroxide to produce a foam suitable for subsequent application to fibrous substrates.

As an alternative step (b), the foam can be applied by a doctor blade or any other suitable method with no removal of excess foam normally being needed. However, this does not preclude the removal of such by any art-known means such as those described in step (b) above. Steps (c) through (e), describing the respective processes for heating, washing, and final drying, are identical for both the foam and solvent application processes.

In the following examples, all parts and percentages are by weight. Analyses for carbon, hydrogen, magnesium, and acetate were conducted by independent commercial laboratories by standard and widely accepted analytical procedures. Analyses for peroxide oxygen (—O—O—) on the reaction products and on modified fibrous substrates were conducted iodometrically by a procedure similar to that of Wentz and Cates, *Textile Research J.* 45:691 (1975), as follows: The solid (0.04 gram) or fibrous substrate (0.40 gram) is placed in a flask to which the following is added: 50 ml deionized water, 1 ml of saturated potassium iodide (22.5 grams potassium iodide in 15 ml of water), and 1 ml of 37% aqueous hydrochloric acid. The flask is then lightly stoppered, heated on a steam cone for 10 minutes, and then titrated with a 0.1N standardized solution of sodium thiosulfate until colorless. Percent peroxide oxygen=0.16(mls of 0.1N $Na_2S_2O_3$)/grams of sample.

Infrared spectra of the solid reactants (magnesium acetate tetrahydrate and calcium acetate monohydrate) of the solid products (various magnesium peroxyacetate compositions and calcium peroxyacetate compositions) were determined by mixing about 1.5 mg of the solid with 250 mg of spectroscopic grade potassium bromide to form a disk that was evaluated with an infrared spectrophotometer interfaced to a computer.

Thermal behavior (melting, stability, and decomposition) of the reactants and products was determined from 0°–500° C. by differential scanning calorimetry at a heating rate of 10° C./minute.

Antibacterial activity of untreated and modified textiles or fibrous substrates were quantitatively determined by a commercial laboratory by method AATCC-100-1989 using the representative gram-positive bacteria *Staphylococcus aureus* and gram-negative bacteria *Klebsiella pneumoniae*.

EXAMPLE 1

Preparation of Reaction Products from Hydrogen Peroxide and Magnesium Acetate (Mole Ratio of 7:1)

Magnesium acetate tetrahydrate (10.0 grams, 0.047 mole) was dissolved in 30% aqueous hydrogen peroxide (37.0 grams, 0.33 mole) in a beaker. The resultant solution was poured into a glass dish that was subsequently placed into a preheated force draft oven (200° C.). The reaction is characterized by the production of foam due to evolution of gas. Thus, it is necessary to use a dish or container of sufficient volume and surface area to contain the foam produced. After 20 minutes, with intermittent breaking of the foam, the solution had evaporated to dryness to give a white, flaky reaction product. The dish was removed from the oven and the residue ground into a powder with a wide spatula. The dish containing the powder was heated in the oven an additional 5 minutes at 200° C. to ensure complete drying. The water-insoluble reaction product (derived from mole ratio of 7:1 hydrogen peroxide:magnesium acetate tetrahydrate) was purified by washing with absolute ethanol and suction filtration (four times). The product was then dried in a vacuum oven at reduced pressure to constant weight at 90° C.

Chemical analyses for a molar ratio of reaction product derived from the above 7:1 mole ratio observed (calculated) were: 27.8% carbon (27.9%), 4.5% hydrogen (3.9%), 18.6% magnesium (20.8%), 5.7% peroxide (6.2%), and 59.3% acetate (67.0%) corresponding to displacement of acetate groups to give a water-insoluble product containing 50% anhydrous magnesium acetate and 50% magnesium peroxyacetate. The infrared spectra of the reaction product exhibited absorption peaks or bands at 1600 and 1430 cm$^{-1}$ (characteristic of —O—O— bonds that were also observed for a commercial sample of magnesium peroxide); unreacted magnesium acetate tetrahydrate did not show absorption in these regions. Thermal analysis by differential scanning calorimetry (DSC) of the reaction product was characterized by endothermic melting at 376° C. (major peak) and 151° C. (minor peak due to melting of dehydrated magnesium acetate tetrahydrate). In contrast, the starting material (magnesium acetate tetrahydrate) exhibited major endothermic melting at 73° C. (due to the tetrahydrate) and 156° C. (dehydrated magnesium acetate tetrahydrate).

EXAMPLE 2

Preparation of Reaction Products from Hydrogen Peroxide and Magnesium Acetate (Mole Ratio of 2:1)

The preparation of a water-insoluble product derived from mole ratio of 2:1 (hydrogen peroxide:magnesium acetate tetrahydrate) was carried out by a procedure similar to Example 1 by adding magnesium acetate tetrahydrate (50.0 grams, 0.23 mole) to 30% aqueous hydrogen peroxide (50.0 grams, 0.44 mole) in a beaker. The glass dish containing the solution was placed in a preheated force draft oven at 200° C. until it was nearly all dry; the dish was removed from the oven, its contents mixed well, then reheated in the oven until a flaky, white residue remained. The residue was broken into powder form and oven dried at 200° C. for 5 minutes to insure complete drying. The reaction product was washed with ethanol and dried as described in Example 1. Peroxide analysis for the reaction product was 1.37%.

EXAMPLE 3

Preparation of Reaction Products from Hydrogen Peroxide and Magnesium Acetate (Mole Ratio of 16:1)

The preparation of a water-insoluble product derived from a mole ratio of 16:1 (hydrogen peroxide:magnesium acetate tetrahydrate) was carried out by a procedure similar to that of Example 1.

Magnesium acetate tetrahydrate (10.0 grams, 0.047 mole) was added to 30% aqueous hydrogen peroxide (84.4 grams, 0.745 mole) in a beaker. A glass dish containing the solution was placed in a preheated force draft oven at 200° C. until it was nearly dry. The dish was removed from the oven, its contents mixed well, then reheated in the oven at 200° C. until a flaky, white residue remained. The residue was broken into powder form and oven dried at 200° C. for 5 minutes to ensure complete drying. The reaction product was washed with ethanol and dried as described in Example 1.

Chemical analyses for a molar ratio of reaction product derived from the above 16:1 mole ratio, observed (calculated) were: 20.6% carbon (20.6%), 3.2% hydrogen (3.5%), 22.6% magnesium (20.9%), 14.3% peroxide (13.8%), and 52.7% acetate (50.7%) corresponding to displacement of acetate groups to give a water-insoluble product containing magnesium peroxyacetate denoted as MPA or

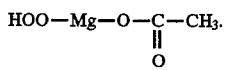

Infrared spectra of this reaction product was characterized by the same absorption bands of the reaction product described in Example 1. DSC analysis produced equal amounts of exothermic decomposition at 348° C. (due to the peroxide group) and endothermic melting at 371° C.

Infrared spectroscopy was carried out (in solid state as KBr disc) for:

(a) starting material-magnesium acetate tetrahydrate
(b) MPA product
(c) reagent grade magnesium peroxide [MgO$_2$(MgO)$_n$]
(d) reagent grade magnesium hydroxide Mg(OH)$_2$
(e) calcium acetate monohydrate
(f) reaction product of (e) with hydrogen peroxide—designated CPA
(g) calcium hydroxide.

pH measurements of the above 7 compositions and compounds were also conducted.

Interpretation of infrared(IR) spectra:

(1) There are distinct and substantial differences of the IR spectra of the starting material (magnesium acetate tetrahydrate) and of the reaction product.
(2) The IR spectra of reagent grade magnesium peroxide and of magnesium hydroxide were also run to compare absorption peaks in these known materials with that of the magnesium peroxyacetate.
(3) The significant reduction of the —OH absorption peak of the starting material at 3500 cm$^{-1}$ and its shift to 3400 cm$^{-1}$ in the magnesium peroxyacetate is consistent with the loss of hydrated water and formation of a Mg—OOH structure. Moreover, the lack of any peak (intense or weak) at 3750 cm$^{-1}$ in the magnesium peroxyacetate indicates that there is no Mg—OH structure present. Mg(OH)$_2$ shows a sharp and intense absorption at this wavenumber.

(4) The appearance of intense peaks at 1440 and 1540 cm$^{-1}$ in the MPA is quite similar to that observed in the known magnesium peroxide structure and is quite indicative of a Mg—OO— structure.

(5) Infrared spectra of calcium acetate monohydrate and its reaction product with hydrogen peroxide (denoted as CPA) are practically indistinguishable, indicating little or no reaction. This is in marked contrast to the magnesium peroxyacetate product derived from the analogous magnesium acetate tetrahydrate with hydrogen peroxide.

The pH's of magnesium peroxyacetate(MPA), starting materials used for its preparation, and related compounds were measured. The solids (0.5 g. of each) were added to 15 mL of deionized water and measured on a pH meter. See table below.

pH of MPA and Related Materials

| Material | Chemical Formula | pH |
| --- | --- | --- |
| Magnesium acetate tetrahydrate | Mg(C$_2$H$_3$O$_2$)$_2$.4H2O | 8.8 |
| Magnesium peroxyacetate (MPA) | Mg(C$_2$H$_3$O$_2$)(OOH) M.W. 116 | 9.6 |
| Magnesium hydroxide | Mg(OH)$_2$ | 9.9 |
| Magnesium peroxide | MgO$_2$.(MgO)$_n$ | 10.2 |
| Calcium acetate monohydrate (CA) | Ca(C$_2$H$_3$O$_2$)$_2$.H$_2$O | 7.6 |
| Reaction product of CA + H$_2$O$_2$ | — | 8.1 |
| Calcium hydroxide | Ca(OH)$_2$ | 11.9 |

The pH measurements on the same compounds and compositions that were evaluated by infrared spectra are indicative of the following:

The increase in the pH from 8.8 to 9.6 (respectively for the starting material and the product MPA) is consistent with a Mg—OOH structure rather than a Mg—OH structure because the known magnesium peroxide/oxide has a pH even more alkaline than that of Mg(OH)$_2$. It is plausible that small amounts of MgO formed as a byproduct could raise the pH of the MPA somewhat.

No conclusions can be made about the CPA relative to the starting material based only on pH, since IR spectra are almost identical and there is very little active oxygen in the CPA compared to substantial amounts of active oxygen in the magnesium analog MPA.

Therefore, on the basis of elemental analysis (% C, H, Mg, acetate), molecular weight determination, IR spectra, and pH, the structure postulated for the MPA is the most plausible, that is, displacement of one of the acetate groups by a —OOH group with trace amounts of MgO that would elevate the pH by the observed amount.

Active oxygen or peroxide analysis for molar ratios of hydrogen peroxide to magnesium acetate tetrahydrate in ranges from 12:1 to 20:1 resulted in very little difference in this analysis. Thus, the 16:1 molar ratio was selected for detailed elemental analysis and evaluation.

Thus, the correct "trivial" name for the new reaction product would be magnesium peroxyacetate (MPA).

Thermal scans were also run to provide additional analytical data of four different ratios of magnesium acetate tetrahydrate/hydrogen peroxide for the new composition of matter described herein that has antibacterial activity when applied to fibrous substrates. The reaction ratio of 1:7 produced a marked change in the thermal profile (characteristic peak at 376° C. compared to melting of starting material at 73° C.). At higher ratios, exothermic decomposition occurs (at 340°–350° C.). Thermal scans of known magnesium peroxide and zinc acetate/peroxide are very different from the magnesium reaction products. The zinc compounds undergo exothermic decomposition at much lower temperatures (ca. 238° C.) than the magnesium peroxyacetate compositions. Finally, there was very little difference between the thermal scans of calcium acetate monohydrate and its reaction product with hydrogen peroxide, in marked contrast to the magnesium acetate reaction product scans.

EXAMPLE 4

Preparation of Reaction Products from Hydrogen Peroxide and Magnesium Acetate (Mole Ratio of 30:1)

The preparation of a water-insoluble product derived from a mole ratio of 30:1 (hydrogen peroxide:magnesium acetate tetrahydrate) was carried out by a procedure similar to Example 1. Magnesium acetate tetrahydrate (10.0 grams, 0.047 mole) was added to 30% aqueous hydrogen peroxide (158.3 grams, 1.40 mole) in a Pyrex™ glass dish. The dish containing the solution was placed in a preheated force draft oven at 200° C. for 15 minutes. It was then removed from the oven, its contents mixed well, and reheated in the oven at 90° C. until significant foam evolution occurred. The dish was again placed in the oven at 90° C. until all liquid had evaporated, removed to mix its contents, then subjected to a final drying step at 90° C. for 15 minutes. The reaction product was washed with ethanol and dried as described in Example 1.

Chemical analyses for a molar ratio of reaction product derived from the above 30:1 mole ratio observed (calculated) were: 15.8% carbon (14.9%), 3.0% hydrogen (3.1%), 22.7% magnesium (22.4%), 20.4% peroxide (19.8%) and 31.7% acetate (36.8%) corresponding to displacement of acetate groups to give a water-insoluble product containing 67% magnesium peroxyacetate, and 33% magnesium dihydroperoxide. The infrared spectrum of this reaction product was again characterized by the same absorption bands observed for the reaction product described in Example 1. DSC analysis produced only exothermic decomposition at 342° C. (due to appreciable concentrations of the peroxide group).

EXAMPLE 5

Preparation of Reaction Products from Hydrogen Peroxide and Magnesium Acetate (Mole Ratio of 40:1)

The preparation of a water-insoluble product derived from a mole ratio of 40:1 (hydrogen peroxide:magnesium acetate tetrahydrate) was carried out by a procedure similar to Example 3. Magnesium acetate tetrahydrate (15.1 grams, 0.07 mole) was added to 30% aqueous hydrogen peroxide (318.6 grams, 2.8 mole) in a Pyrex™ glass dish. The dish containing the solution was placed in a preheated force draft oven at 120° C. for 45 minutes at which time foam was beginning to form. The dish was removed and the oven set at 90° C. The dish was replaced in the 90° C. oven for 30 minutes during which time it was removed, mixed, and replaced at 10 minute intervals. The resultant dry, flaky material was ground to a powder and oven-dried an additional 10 minutes at 120° C.

Chemical analyses for a molar ratio of reaction product derived from the above 40:1 mole ratio, observed (calculated) were: 12.2% carbon (7.4%), 2.1% hydrogen (2.7%), 23.9% magnesium (24.9%), 29.0% peroxide (27.2%), and 20.8% acetate (18.1%) corresponding to displacement of acetate groups to give a water-insoluble product containing 30% magnesium peroxyacetate, and 70% magnesium dihydroperoxide. The infrared spectra and DSC scans of this reaction product were similar to those of the reaction product described in Example 4—absorption bands at 1600 and 1430 cm$^{-1}$ in the infrared spectra and exothermic decomposition at 350° C. due to presence of peroxide groups.

EXAMPLE 6

(Comparative Example)

Attempted Preparation of Peroxy-containing Products from Reaction of Hydrogen Peroxide with Calcium Acetate (Mole Ratios 7:1 and 28:1)

Calcium acetate monohydrate (5.0 grams, 0.028 mole) was dissolved in 30% hydrogen peroxide (22.5 grams, 0.20 mole) in a Pyrex™ glass dish and brought to dryness in a forced draft oven at 150° C. The mixture was powdered and dried an additional 5 minutes at 150° C. The peroxide content of the 7:1 product was only 2.25%. The peroxide content of the product was again only 2.27% when its mole ratio was increased to 28:1 (calcium acetate monohydrate, 5.00 grams, 0.028 mole: 30% hydrogen peroxide, 90.00 grams, 0.80 mole) and it was dried under the same conditions. Thermal analysis and infrared spectra of product derived from a 28:1 ratio demonstrated that there was negligible or no reaction, since the thermal characteristics (endotherms associated with melting and dehydration) and infrared spectra absorption bands were identical in starting material (calcium acetate monohydrate) and product.

EXAMPLE 7

Application of Reaction Products from Hydrogen Peroxide and Magnesium Acetate (Mole Ratio of 40:1) to Cotton Desized, scoured, and bleached 80×80 cotton printcloth (98.7 g/m$^2$) was immersed in an aqueous suspension containing 16.5% by weight of the reaction product prepared in Example 5 (40:1 mole ratio of hydrogen peroxide:magnesium acetate tetrahydrate) until thoroughly wet, passed through squeeze rolls of a motorized padder at a pressure of 40 psi, adjusted to give a wet pickup of 85%, and then cured in a laboratory-type convection oven that simulated large scale commercial production for 4 minutes at 125° C.

The fibrous substrate was then washed in hot running water at 60° C. for 10 minutes and oven-dried for 4 minutes at 125° C. The modified fibrous substrate had a weight gain of 7% and a peroxide oxygen content of 1.64%. It was bactericidal because it decreased the bacterial colony growth by 99.9% when evaluated by the quantitative AATCC 100 test against both representative gram-positive (*Staphylococcus aureus*) and gram-negative (*Klebsiella pneumoniae*) bacteria. Comparable evaluation of an untreated cotton fibrous substrate demonstrated no reduction in growth of either type of bacterial colony.

After the above modified fibrous substrate had been laundered fifty times in an automatic clothes washer and tumble dryer, it still had an active oxygen content of 0.43% and was still 99.3% effective in reducing bacterial growth of both types of bacteria.

EXAMPLE 8

Application of Reaction Products from Hydrogen Peroxide and Magnesium Acetate (Mole Ratio of 16:1) to Cotton/Polyester Blends 50/50 Cotton/polyester sheeting (136 g/m$^2$) was immersed in an aqueous suspension containing 16.5% by weight of the reaction product prepared in Example 3 (16:1 mole ratio of hydrogen peroxide:magnesium acetate tetrahydrate) until thoroughly wet. It was then squeezed through the rolls of a motorized padder at a pressure of 40 psi, adjusted to give a wet pickup of 78%, and cured for 4 minutes at 125° C. in a laboratory-type convection oven that simulated large scale commercial production. The fibrous substrate was then washed in hot running water at 60° C. for 10 minutes and oven-dried for 4 minutes at 125° C. The modified blend fibrous substrate had a weight gain of 4% and a peroxide oxygen content of 1.13%. its bacterial colony growth decreased by 99.90% when evaluated by the quantitative AATCC 100 test against both representative gram-positive (*Staphylococcus aureus*) and gram-negative (*Klebsiella pneumonias*) bacteria. Comparable evaluation of an untreated cotton/polyester fibrous substrate demonstrated no reduction in growth of either type of bacterial colony.

After the above modified fibrous substrate had been laundered twenty times in an automatic clothes washer and tumble dryer, it still had a peroxide oxygen content of 0.35% and was still 99.90% effective in reducing bacterial growth of both types of bacteria.

EXAMPLE 9

Application of Reaction Products from Hydrogen Peroxide and Magnesium Acetate (Mole Ratio of 7:1) to Cotton The untreated cotton fibrous substrate described in Example 7 was immersed in an aqueous suspension containing 16.7% by weight of the reaction product prepared in Example 1 (7:1 mole ratio of hydrogen peroxide:magnesium acetate tetrahydrate) until thoroughly wet. It was then squeezed through rolls of a motorized padder at a pressure of 40 psi, adjusted to give a wet pickup of 91%, and then cured for 3 minutes at 120° C. in a laboratory-type convection oven that simulated large scale commercial production. The fibrous substrate was then washed in hot running water at 60° C. for 10 minutes and oven-dried for 3 minutes at 120° C. The modified cotton fibrous substrate had a weight gain of 1% and a peroxide oxygen content of 0.31%. Its bacterial colony growth decreased by 99.9% when evaluated by the quantitative AATCC 100 test against both representative gram-positive (*Staphylococcus aureus*) and gram-negative (*Klebsiella pneumoniae*) bacteria. Comparable evaluation of an untreated cotton fibrous substrate demonstrated no reduction in growth of either type of bacterial colony.

After the above modified fibrous substrate had been laundered ten times in an automatic clothes washer and tumble dryer, it still had an active oxygen content of 0.12% and was still 99.9% effective in reducing bacterial growth of both types of bacteria.

EXAMPLE 10

Application of Reaction Products from Hydrogen Peroxide and Magnesium Acetate (Mole Ratio of 40:1) to Polypropylene Woven polypropylene fibrous substrate (169.2 g/m$^2$) was immersed in a 3% aqueous H$_2$O$_2$ suspension containing 16.6% by weight of the reaction product of Example 5 (40:1 mole ratio of hydrogen peroxide:magnesium acetate tetrahydrate) until thoroughly wet. It was then squeezed through rolls of a motorized padder at a pressure of 40 psi, adjusted to give a wet pickup of 54%, and cured for 4 minutes at 125° C. in a laboratory-type convection oven that simulated large scale commercial production. The fibrous substrate was then washed in hot running water at 60° C. for 10 minutes and oven-dried for 4 minutes at 125° C. The modified fibrous substrate had a weight gain of 3% and a peroxide oxygen content of 0.58%. Bacterial colony growth decreased by 99.9% when evaluated by the quantitative AATCC 100 test against both representative gram-positive (*Staphylococcus aureus*) and gram-negative (*Klebsiella pneumoniae*) bacteria. Comparable evaluation of an untreated polypropylene fibrous substrate demonstrated no reduction in growth of either type of bacterial colony.

After the above modified fibrous substrate had been laundered five times in an automatic clothes washer and tumble dryer, it still had a peroxide oxygen content of 0.16% and was still 99.1% effective in reducing bacterial growth of both types of bacteria.

EXAMPLE 11

Application of Reaction Products from Hydrogen Peroxide and Magnesium Acetate (Mole Ratio of 16:1) to Nonwoven Paper A nonwoven paper towel reinforced with polyamide (65.1 g/m$^2$) was immersed in an aqueous suspension containing 16.7% by weight of the reaction product of Example 3 (16:1 mole ratio of hydrogen peroxide:magnesium acetate tetrahydrate) until thoroughly wet. It was then squeezed through rolls of a motorized padder at a pressure of 40 psi, adjusted to give a wet pickup of 100%, and cured for 3 minutes at 120° C. in a laboratory-type convection oven that simulated large scale commercial production. The paper towel was then washed in hot running water at 60° C. for 10 minutes and oven-dried for 3 minutes at 120° C. The modified paper towel had a weight gain of 1.9% and a peroxide oxygen content of 0.65%. Bacterial colony growth decreased by 99.9% as evaluated by the quantitative AATCC 100 test against both representative gram-positive (*Staphylococcus aureus*) and gram-negative (*Klebsiella pneumoniae*) bacteria. Comparable evaluation of an untreated paper towel fibrous substrate demonstrated no reduction in growth of *Klebsiella pneumoniae* and only 63% reduction in growth of *Staphylococcus aureus*.

EXAMPLE 12

Application of Reaction Products as Foam (from Hydrogen Peroxide and Magnesium Acetate—Mole Ratio of 16:1—in 30% Hydrogen Peroxide) to Nonwoven Paper A nonwoven paper towel reinforced with polyamide (65.1 g/m$^2$) was treated with a foam generated from an aqueous 30% H$_2$O$_2$ solution containing 16.7% of the reaction product of Example 3, which was applied with a doctor blade, to a wet pickup of 81%. The modified paper towel had a weight gain of 1.5% and a peroxide oxygen content of 0.53% after it was cured for 3 minutes at 120° C. and washed and dried as described in Example 11. This modified paper towel also reduced bacterial growth by 99.9% against the two representative bacteria used in the AATCC 100 test.

EXAMPLE 13

Application of Reaction Products from Hydrogen Peroxide and Calcium Acetate (Mole Ratio of 7:1) to Cotton The untreated cotton fibrous substrate described in Example 7 was immersed in an aqueous suspension containing 16.7% by weight of reaction product prepared in Example 6 (7:1 mole ratio of hydrogen peroxide:calcium acetate monohydrate) until thoroughly wet. It was then squeezed through rolls of a motorized padder at a pressure of 40 psi, adjusted to give a wet pickup of 86%, and then cured for 3 minutes at 120° C. in a laboratory-type convection oven that simulated large scale commercial production. The fibrous substrate was then washed in hot running water at 60° C. for 10 minutes and oven-dried for 3 minutes at 120° C. The treated cotton fibrous substrate had neither a weight gain nor any peroxide oxygen present.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A solid water-insoluble compound possessing a structural formula selected from the group consisting of $$CH_3\overset{O}{\overset{\|}{C}}-O-Mg-OOH \qquad (I)$$

and $$Mg(OOH)_2. \qquad (II)$$

2. The compound of claim 1 which is magnesium peroxyacetate and which possesses the structural formula $$CH_3\overset{O}{\overset{\|}{C}}-O-Mg-OOH.$$

3. The compound of claim 1 which is magnesium dihydroperoxide and which possesses the formula $$Mg(OOH)_2.$$

4. An antibacterial composition comprising one or more solid water-insoluble compounds selected from the group consisting of magnesium peroxyacetate and magnesium dihydroperoxide.

5. The composition of claim 4 possessing a peroxide oxygen content ranging from about 1% to about 30% by weight of said composition.

6. A solid water-insoluble antibacterial composition containing from about 1% to about 30% peroxide oxygen by weight of said composition in the form of magnesium-peroxy reaction products produced by the steps of:
   (a) preparing an aqueous solution comprising from about 15% to about 29% by weight hydrogen peroxide and from about 5% to about 50% by weight, based on magnesium acetate tetrahydrate, of magnesium acetate in either its anhydrous or tetrahydrate form, and
   (b) removing the water to yield a solid comprising magnesium peroxyacetate, magnesium dihydroperoxide, or a combination thereof.

7. The antibacterial composition of claim 6 wherein the water is removed through the application of heat and/or the reduction of pressure.

8. A process for the preparation of stable, bactericidal reaction products, containing from about 1% to about 30% peroxide oxygen by weight of said reaction products, comprising:
   (a) preparing an aqueous solution comprising from about 15% to about 29% by weight hydrogen peroxide and from about 5% to about 50% by weight, based on magnesium acetate tetrahydrate, of magnesium acetate in either its anhydrous or tetrahydrate form, and (b) removing the water to yield a solid comprising magnesium peroxyacetate, magnesium dihydroperoxide, or a combination thereof.

9. The process of claim 8 wherein the water removal of step (b) is accomplished through the application of heat and/or the reduction of pressure.

10. The process of claim 8 further comprising the steps of:
   (c) washing the solid product of step (b);
   (d) filtering the solid product; and
   (e) drying the solid product.

11. A process for rendering a fibrous substrate bacteriostatic and/or bactericidal comprising:
   (a) immersing the fibrous substrate in an aqueous dispersion comprising from about 10% to about 17% by weight of the antibacterial composition of claim 6 and from about 0% to about 27% by weight of hydrogen peroxide; and
   (b) drying the fibrous substrate whereby the magnesium-peroxy reaction products from said antibacterial composition are deposited on the substrate.

12. The process of claim 11 wherein the aqueous dispersion is applied at a wet-pickup ranging from about 10% to about 200% by weight.

13. The process of claim 11 further comprising the steps of washing and drying the fibrous substrate.

14. The process of claim 11 wherein the fibrous substrate is selected from the group consisting of cellulose, wool, polyester, polyamide, polypropylene, glass; and blends thereof.

15. A process for applying the antibacterial composition of claim 6 to fibrous substrates to render the fibrous substrates bacteriostatic and/or bactericidal comprising:
   (a) applying an aqueous foam to the fibrous substrate, said foam containing from about 10% to about 20% by weight of the antibacterial composition and from about 3% to about 27% by weight hydrogen peroxide; and
   (b) drying the fibrous substrate whereby the magnesium-peroxy reaction products from said antibacterial composition are deposited on the substrate.

16. The process of claim 15 further comprising the steps of washing and drying the fibrous substrate.

17. The process of claim 15 further comprising the step of removing only excess foam from the fibrous substrate prior to step (b).

18. The process of claim 15 wherein the fibrous substrate is selected from the group consisting of cellulose, wool, polyester, polyamide, polypropylene, glass, and blends thereof.

19. A fibrous substrate rendered bacteriostatic and/or bactericidal by contacting said fibrous substrate with the composition of claim 4.

20. A fibrous substrate rendered bacteriostatic and/or bactericidal by the process of claim 11.

21. A fibrous substrate rendered bacteriostatic and/or bactericidal by the process of claim 15.

* * * * *